(12) United States Patent
Whipple

(10) Patent No.: US 7,887,325 B2
(45) Date of Patent: Feb. 15, 2011

(54) IMPLANT-DRIVER ASSEMBLY

(75) Inventor: Dale Whipple, East Taunton, MA (US)

(73) Assignee: Keystone Dental, Inc., Burlington, MA (US)

( * ) Notice: Subject to any disclaimer, the term of this patent is extended or adjusted under 35 U.S.C. 154(b) by 144 days.

(21) Appl. No.: 12/062,782

(22) Filed: Apr. 4, 2008

(65) Prior Publication Data
US 2009/0253098 A1 Oct. 8, 2009

(51) Int. Cl.
*A61C 3/00* (2006.01)
(52) U.S. Cl. ........................................ 433/163; 433/174
(58) Field of Classification Search ................ 433/163, 433/141, 172–176, 201.1
See application file for complete search history.

(56) References Cited

U.S. PATENT DOCUMENTS

| | | | | |
|---|---|---|---|---|
| 6,086,371 | A * | 7/2000 | Bassett et al. ................ | 433/173 |
| 6,206,696 | B1 * | 3/2001 | Day ............................ | 433/141 |
| 6,217,331 | B1 * | 4/2001 | Rogers et al. ................ | 433/173 |
| 6,217,332 | B1 * | 4/2001 | Kumar ......................... | 433/173 |
| 6,247,932 | B1 * | 6/2001 | Sutter ......................... | 433/173 |
| 6,315,562 | B1 * | 11/2001 | Kumar ......................... | 433/173 |
| 6,416,324 | B1 * | 7/2002 | Day ............................ | 433/173 |
| 6,561,805 | B2 * | 5/2003 | Kumar ......................... | 433/174 |
| 7,033,174 | B2 * | 4/2006 | Giorno ........................ | 433/174 |
| 7,160,109 | B2 * | 1/2007 | Gervais et al. .............. | 433/141 |
| 2001/0019816 | A1 | 9/2001 | Kumar | |
| 2003/0224325 | A1 * | 12/2003 | Kumar et al. ................ | 433/163 |
| 2007/0072148 | A1 * | 3/2007 | Memmolo et al. ........... | 433/141 |

FOREIGN PATENT DOCUMENTS

WO 0009031 2/2000

OTHER PUBLICATIONS

PCT/US2009/034258 International Search Report dated May 13, 2009.

* cited by examiner

*Primary Examiner*—Cris L Rodriguez
*Assistant Examiner*—Edward Moran
(74) *Attorney, Agent, or Firm*—Wolf, Greenfield & Sacks, P.C.

(57) ABSTRACT

Disclosed are an implant-driver assembly and an associated method. Generally, the implant-driver assembly includes a driver, an implant and a coupler that affixes the implant to the driver during transport and during insertion of the implant into the jaw of a patient. As shipped, the assembly may take the form of a superassembly with a vial insert that impedes axial movement of the driver, coupler, and implant. Via manual action or assisted with a suitable tool, the coupler may be disengaged to thereby decouple the implant and driver once the implant has been properly positioned. Also disclosed is a method for inserting an implant, the method comprising applying torque to the driver of an implant-driver assembly as disclosed herein.

10 Claims, 5 Drawing Sheets

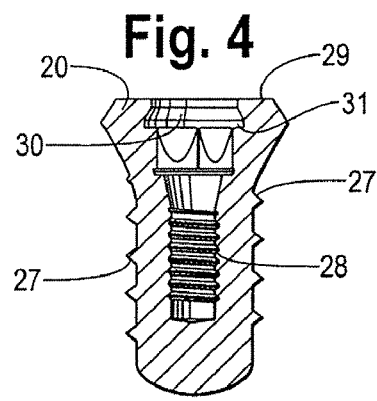
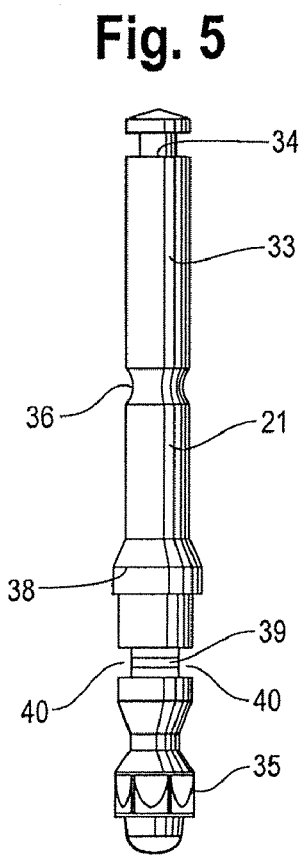
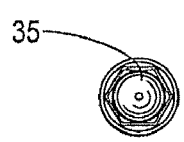
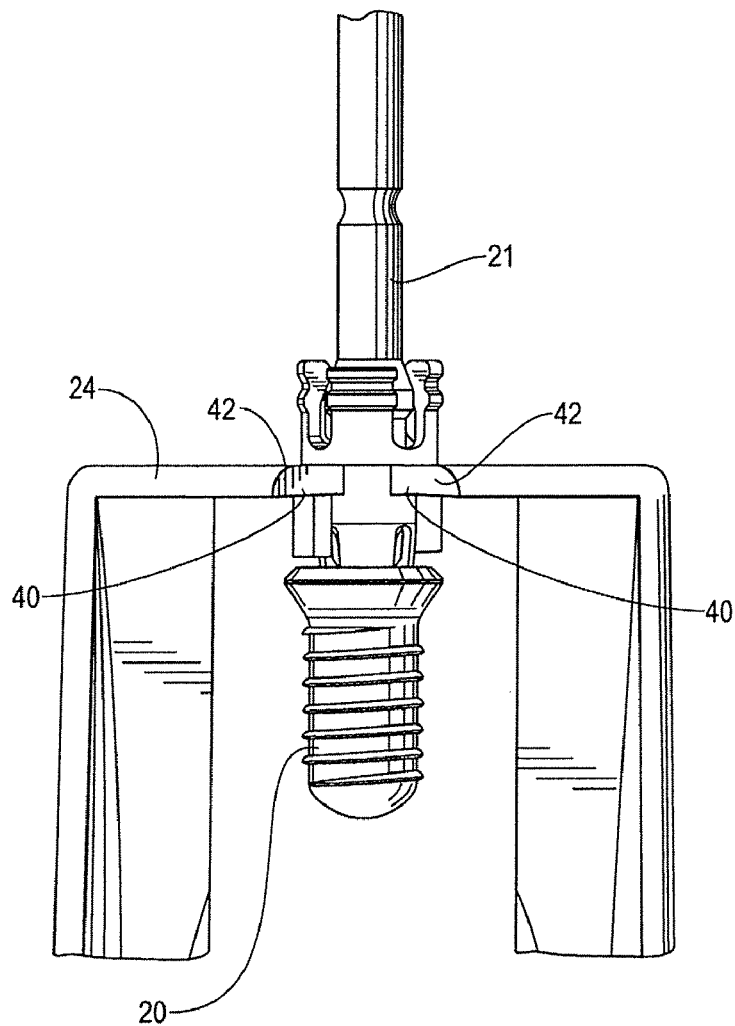

Fig. 11
Fig. 12
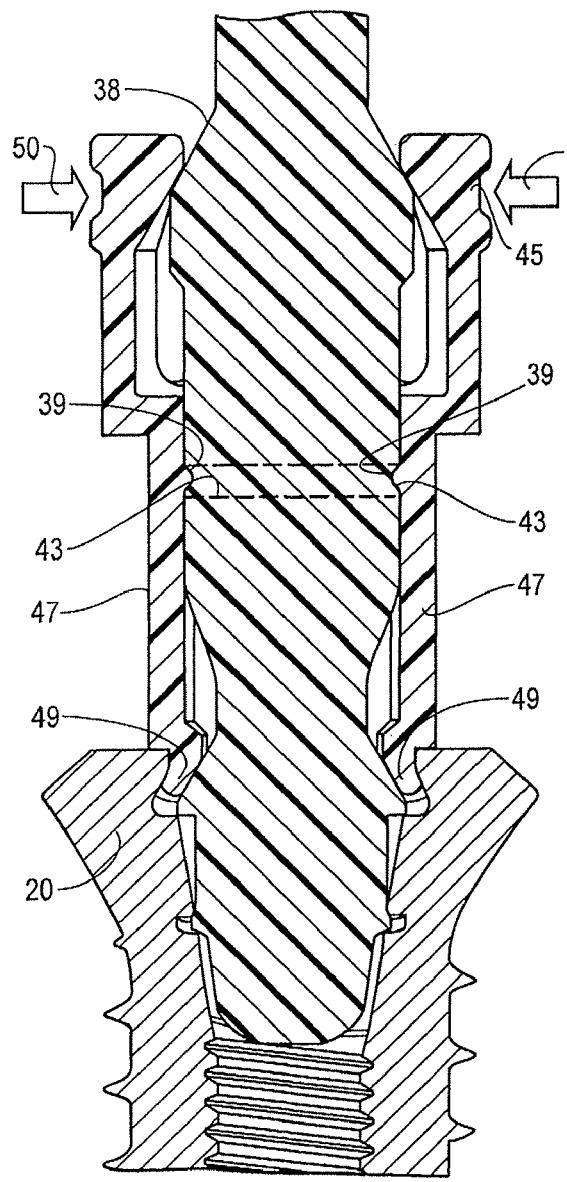
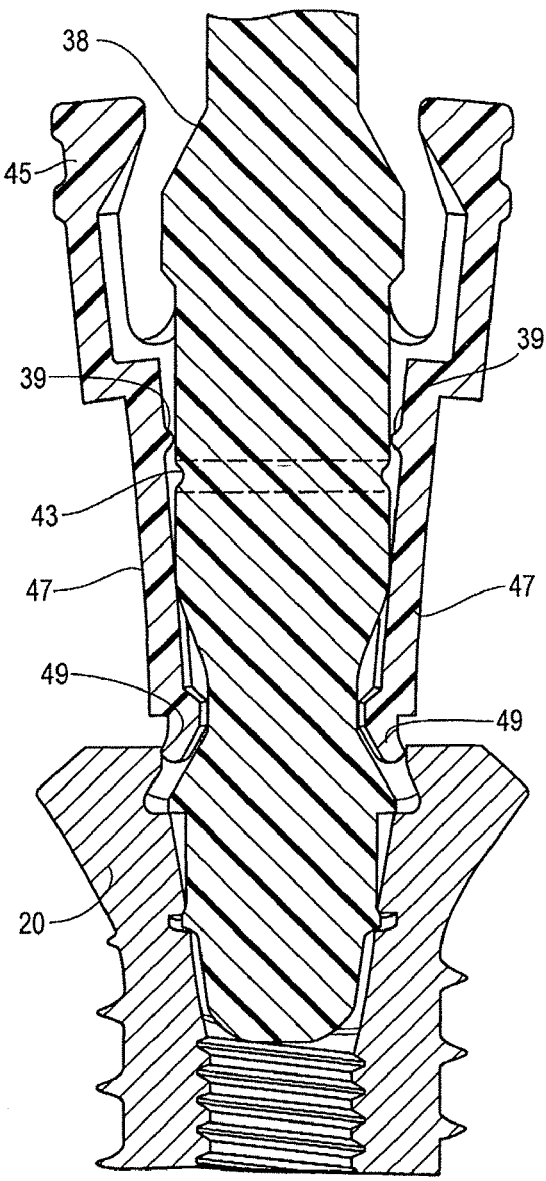

IMPLANT-DRIVER ASSEMBLY

TECHNICAL FIELD OF THE INVENTION

The invention is in the field of medical implants, and in many embodiments is in the field of dental implants.

BACKGROUND OF THE INVENTION

Dental implants long have been known in the art. A dental implant is conventionally a screw-like structure that is threaded both externally and internally. Dental implants are used in the construction of artificial tooth structures in a patient who has lost one or several teeth. Conventionally, a bore is drilled into the jaw of a patient and the implant is driven into the bore. Implants conventionally are made of titanium or a titanium alloy, and, as is known in the art, the titanium implant will osseointegrate into the jaw of a patient over the course of the next several months. Thereafter, other structures are connected to the implant via the internal threads of the implant to form a prosthetic tooth or bridge. Typically, an abutment is connected to the implant via a threaded portion that engages the implant's internal threads, although in some cases a separate abutment screw may be employed. Other structures, such as a prosthetic porcelain tooth or bridge, then are connected to the abutment.

It is known that the external surface of the implant should have certain surface characteristics to assist in osseointegration. During the insertion of the implant, it is known that the implants should not be touched and should not come into contact with certain materials such as plastics. It is also known that care should be taken in driving the implant into the bore in the jaw of the patient. If the driver used for insertion of the implant is worn or is of poor quality, problems can result. Implant manufacturers cannot control the reuse of drivers by dental professionals, even where suitable drivers are provided by the implant manufacturer. Likewise, implant manufacturers cannot control whether an implant is touched prior to insertion.

SUMMARY

The invention provides, in one embodiment, an implant-driver assembly having an implant and a driver. The driver is connected to the implant via a coupler that releasably couples the driver to the implant, whereby the driver may be separated from the implant via disengagement of the coupler after the implant has been inserted into the jaw of the patient. In some embodiments, the implant-driver assembly may be provided in the form of a superassembly that includes a structure that impedes disengagement of the coupler from the implant and that permits the dental professional to manually manipulate the assembly without touching the implant.

This arrangement affords a number of advantages. The dental professional may grasp the assembly at the head of the driver or via the vial structure and thus may avoid physically touching the implant. Because the implant is provided to the dental professional with a driver, the dental professional will generally use the driver provided as part of the assembly, and will not reuse another driver, thus mitigating problems caused by worn or unsuitable drivers.

In another embodiment, a method is provided. The method includes providing an implant-driver assembly, inserting the implant into the jaw of a patient by imparting torque using the driver portion of the implant-driver assembly, and subsequently decoupling the driver and implant once the implant has been inserted into the jaw of the patient. The driver may be driven both clockwise and counterclockwise to thus provide the ability to adjust the depth of the implant in the jaw of the patient and specifically to withdraw the implant if it is inadvertently driven too deeply into the jaw.

Features of the preferred embodiments of the invention are described in more detail hereinbelow and illustrated in the accompanying figures.

BRIEF DESCRIPTION OF THE FIGURES

FIG. 4 is an axial cross sectional view of the implant illustrated in FIG. 3.

FIG. 5 is a front elevation of the driver of the implant assembly illustrated in FIG. 2.

FIG. 6 is a bottom plan view of the driver of the implant-driver assembly illustrated in FIG. 2.

FIG. 7 is a front elevation of a portion of the superassembly illustrated in FIG. 1 showing the engagement of the vial insert, coupler, and driver.

FIG. 11 is an axial cross sectional view of the implant, driver, and coupler shown in FIG. 2, enlarged with respect to FIG. 2 and showing engagement of the coupler with the implant in an engaged position.

FIG. 12 is a front elevation of the implant-driver assembly shown in FIG. 2, enlarged with respect to FIG. 2, and illustrating the coupler after disengagement from the implant.

The views are not intended to be scale figures. Additionally, terms of orientation, such as "front" and "side" are not intended to be limiting, because in practice the implant and implant-driver assembly may be oriented in various positions when in use.

DETAILED DESCRIPTION

Figure 1:
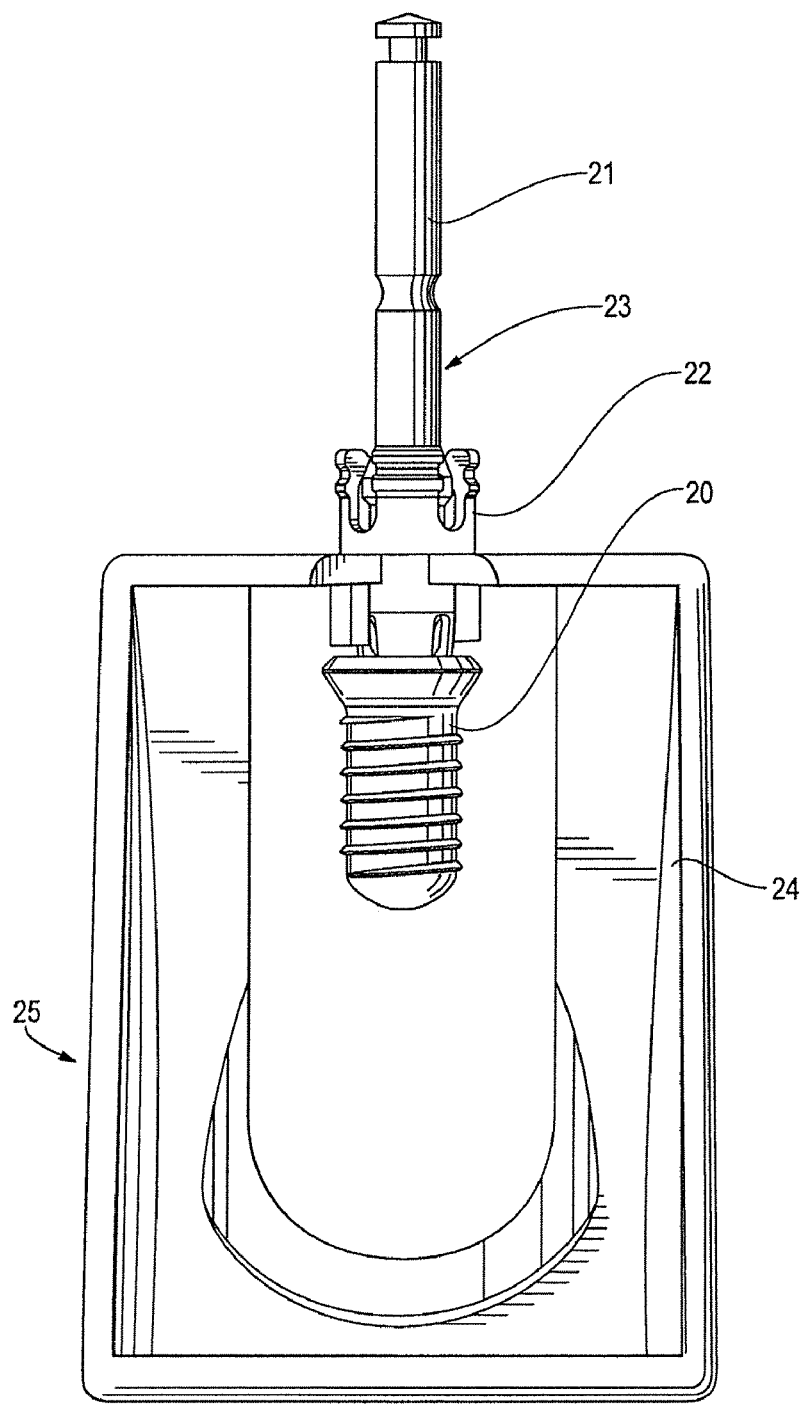
FIG. 1 is a front elevational view of a superassembly that is composed of the implant-driver assembly of one embodiment of the present invention and a vial insert.
Figure 2:
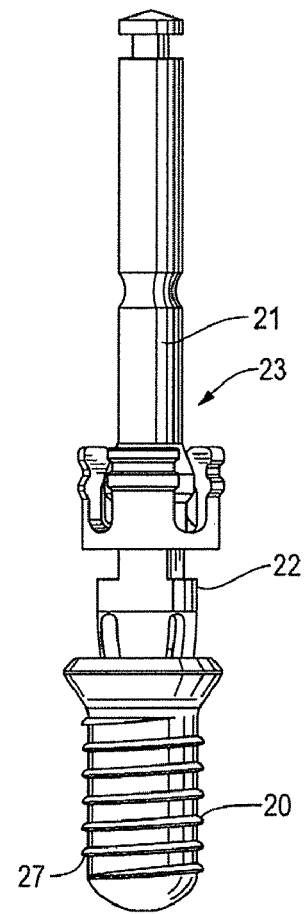
FIG. 2 is a front elevational view of the implant-driver assembly illustrated in FIG. 1.

The implant-driver assembly may be provided to a dental professional in the form of a superassembly as illustrated in FIG. 1. With reference to FIGS. 1 and 2, the implant-driver assembly 23 includes an implant 20, a driver 21, and a coupler 22. The coupler is connected to the driver and to the implant as will be hereafter discussed, such that, during shipment and placement of the implant into the jaw of the patient, the driver 21 is fixed axially with respect to the implant 20. With reference to FIG. 1, a vial insert 24 is connected to the driver 21 and coupler 22 to prevent premature disengagement of the coupler 22 from the implant 20 and driver 21, as hereafter discussed in more detail, thus forming a superassembly 25. The superassembly 25 of FIG. 1 may be contained within an external shipping vial (not shown) for transport from the manufacture to a dental professional. The vial serves as a sterile barrier and shipping package. Upon receipt, the dental professional opens the vial, removes and discards the vial insert 24 and retains the implant-driver assembly 23.

Figure 3:
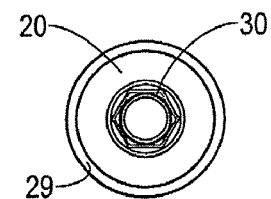
FIG. 3 is a plan view of the implant of the implant-driver assembly illustrated in FIG. 2.
Figure 8:
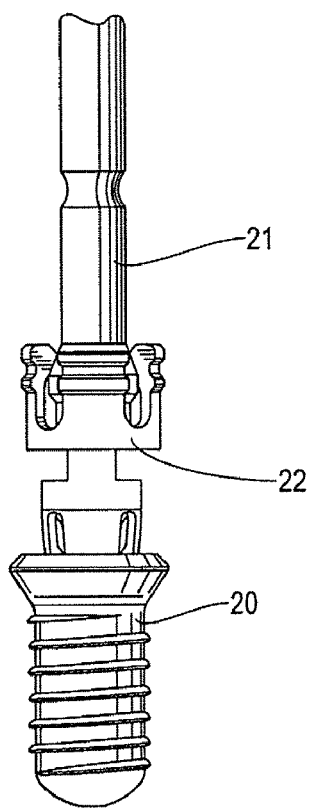
FIG. 8 is a view similar to FIG. 7 but illustrating only the implant-driver assembly.

The configuration of the implant 20 and driver 21 is not critical. In the illustrated embodiment, as best shown in FIGS. 3 and 4, the implant 20 contains external threads 27 and internal implant threads 28 which are intended respectively for threaded engagement with the bone of a patient and with a superstructure, in particular, a screw or thread for retaining an abutment (not shown). The threaded engagement of the implant with the bone of a patient initially may be releasable, but upon osseointegration the threaded engagement generally will not be releasable. The implant 20 includes a supporting ledge 29 that supports the restoration crown (not shown) in a dental restoration. The implant 20 also is provided with a polygonal socket 30 (a hexagonal or other suitably configured socket may be employed) and an annular recess 31, the function of which is described hereinbelow.

Figure 9:
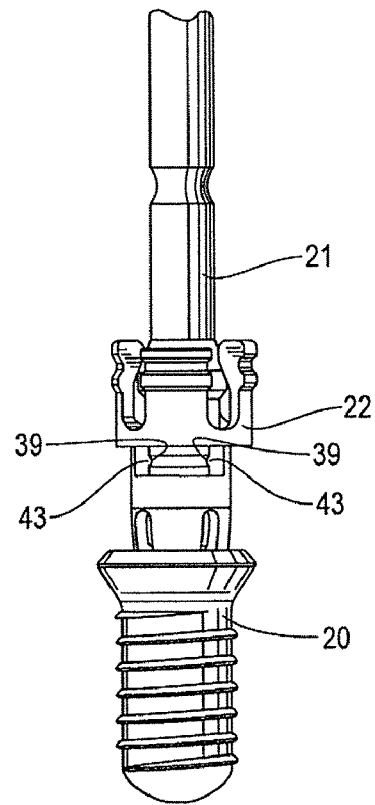
FIG. 9 is a side elevation of the implant-driver assembly shown in FIG. 8, this view being rotated 90° relative to FIG. 8.

With respect to FIGS. 5 and 6, the driver 21 includes a shaft 33 that is provided with a head 34 and a hexagonal drive portion 35. The driver may be retained by a manual or mechanized driving tool (not illustrated). As illustrated, the driver includes a radially recessed area 36 that will cause shearing of the portion of the driver proximal the head 34 if excess torque is applied to the shaft, to thereby protect the internal features of the implant from being damaged by the driver. The driver further is equipped with a flange 38 that has a sloped surface, one function of which will be described hereinbelow. The driver includes a pair of opposing coupler retention slots (one slot 39 shown in FIG. 5) and a pair of opposing notches 40. As best illustrated in FIG. 7, the opposing notches 40 cooperate with detents 42 on the vial insert 24 to impede axial travel of the coupler 22 with respect to the driver 21 when the vial insert is attached. Similarly, as shown in FIG. 9, the retaining slots 39 receive bosses 43 that are integral with the coupler 22.

Figure 10:
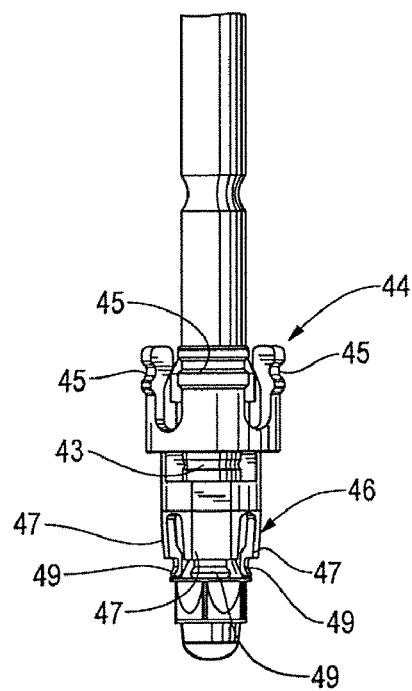
FIG. 10 is a view similar to FIG. 9 but illustrating only the coupler and driver.
Figure 13:
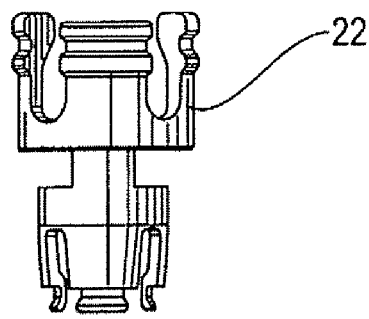
FIGS. 13-15 are respectively a front elevation, a side elevation, and a perspective view of the coupler of the implant-driver assembly shown in FIG. 2.
Figure 14:
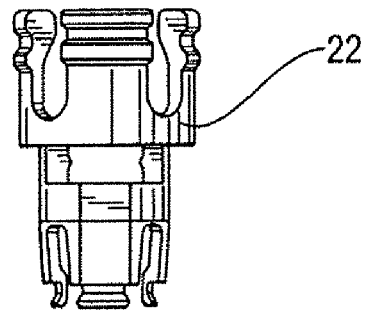
Figure 15:
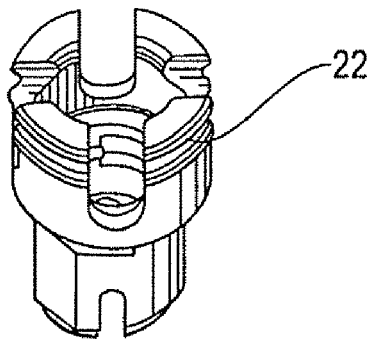

As seen in FIG. 10, the coupler 22 includes an upper collar section 44 and a lower implant engaging section 46. The collar section includes multiple collar fingers 45 each terminating in a collar portion. The implant engaging section 46 is composed of plural fingers 47, each including a radially outwardly protruding portion 49. As best seen in FIG. 11, the protruding portions 49 engage the implant 20 at the annular recess 31. Because the fingers fill the space between the implant 20 and coupler 22, relative axial movement of the implant, driver, and coupler 22 is impeded.

In operation, a dental professional drills a bore into the jaw of the patient and inserts the implant into the bore. Using an appropriate driving mechanism, the dental professional applies torque to the implant to insert the implant into the jaw of the patient. If, during the course of insertion, it is found that the implant has been inserted to a greater depth than desired, reverse torque may be applied to back the implant out of the bore.

Subsequently, as illustrated in FIG. 11, using manual action or assisted with a hemostat or other suitable tool, pressure is applied to the fingers 45 in the direction of arrows 50. Upon application of sufficient pressure, and as illustrated in FIG. 12, the coupler 22 will move axially with respect to the driver 21 and implant 20. Specifically, the collar fingers will slide along the sloped surface of the flange 38 to thereby cause bosses 43 and fingers 47 to axially translate towards the driver head 34. This motion causes disengagement of the bosses 43 from the slots 39 and disengagement of the protruding portions 49 from the radially recessed area 36 of the implant. Via this action the coupler is disengaged, thus enabling removal of the coupler 22 and driver 21 from the implant.

Figure 16:
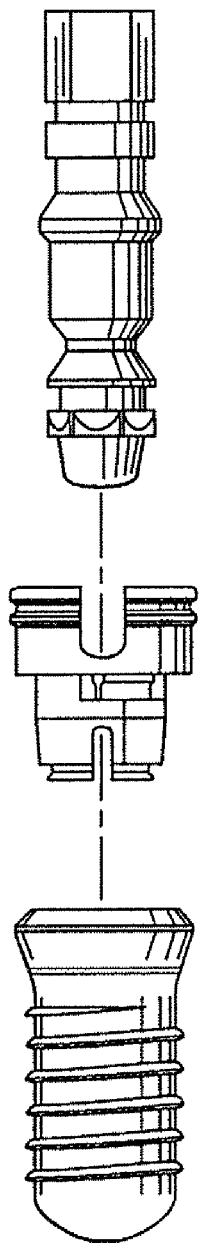
FIG. 16 is an exploded view of an alternative implant-driver assembly.

The implant, driver, and coupler need not be configured precisely as shown in FIGS. 1-15, the assembly of FIG. 16 being one alternative embodiment.

The implant, other than as described herein, is generally convention and is preferably made of titanium or a titanium alloy or another suitable material. The coupler preferably is made of a suitable plastic material. The driver is preferably made of stainless steel or titanium. The vial insert 24 may be made of any suitable material, such as a plastic material.

The invention has been described with particular reference to dental implants, but it is contemplated that the invention is operable with other forms of medical implants.

It is thus seen that an implant-driver assembly according to some embodiments of the invention permits manufacture and transport of an implant to a dental professional and insertion of the implant into the jaw of a patient without the necessity of touching the implant. Moreover, because the driver is effectively integrally associated with the implant during transport and during insertion of the implant, the dental professional will be encouraged to use the driver as supplied, thus mitigating against problems that may arise due to worn or otherwise unsuitable drivers.

Any description of certain embodiments as "preferred" embodiments, and other recitation of embodiments, features, or ranges as being preferred, is not deemed to be limiting, and the invention is deemed to encompass embodiments that are presently deemed to be less preferred. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context.

The invention claimed is:

1. An implant-driver assembly comprising:
   an implant, said implant having external threads permitting threaded engagement with a bone structure;
   a driver having a drive portion at a proximal end, a head at a distal end, and a flange having a sloped surface and positioned between said drive portion and said head; and
   a coupler that releasably couples said driver to said implant and that permits said driver to impart torque to said implant and that further permits removal of said driver from said implant upon disengagement of said coupler, said coupler comprising:
   a collar section including a plurality of fingers adapted to engage the sloped surface of said flange of said driver such that radially inward pressure applied to the plurality of fingers of said collar section disengages said driver from said implant; and
   an implant engaging section positioned proximally to said collar section, wherein said implant engaging section comprises a plurality of fingers each having a protruding portion, said implant being provided with an annular recess such that said protruding portions of said plurality of fingers of said implant engaging section engage the annular recess of said implant to impede relative axial movement between said implant, said driver and said coupler, wherein said plurality of fingers of said implant engaging section of said coupler are released from the annular recess of said implant when radially inward pressure is applied to the plurality of fingers of said collar section of said coupler.

2. An implant-driver assembly according to claim 1 wherein said driver further includes a radially recessed area proximal to the head of said driver that causes shearing of a portion of said driver proximal the head if excess torque is applied to said driver.

3. An implant-driver assembly according to claim 1, further comprising a superassembly that is coupled to said implant-driver assembly by said coupler prior to use of said implant-driver assembly, wherein said coupler prevents axial movement between said implant-driver assembly and said superassembly.

4. An implant-driver assembly according to claim 3, wherein the superassembly comprises a vial insert.

5. An implant-driver assembly according to claim 4, wherein the vial insert includes plural detents each engaging a notch in said driver.

6. A method for inserting a dental implant using an implant-driver assembly, said implant-driver assembly comprising:
    an implant, said implant having external threads permitting threaded engagement with a bone structure;
    a driver having a drive portion at a proximal end, a head at a distal end, and a flange having a sloped surface and positioned between said drive portion and said head; and
    a coupler that releasably couples said driver to said implant and that permits said driver to impart torque to said implant and that further permits removal of said driver from said implant upon disengagement of said coupler, said coupler comprising:
        a collar section including a plurality of fingers adapted to engage the sloped surface of said flange of said driver such that radially inward pressure applied to the plurality of fingers of said collar section disengages said driver from said implant; and
        an implant engaging section positioned proximally to said collar section, wherein said implant engaging section comprises a plurality of fingers each having a protruding portion, said implant being provided with an annular recess such that said protruding portions of said plurality of fingers of said implant engaging section engage the annular recess of said implant to impede relative axial movement between said implant, said driver and said coupler, wherein said plurality of fingers of said implant engaging section of said coupler are released from the annular recess of said implant when radially inward pressure is applied to the plurality of fingers of said collar section of said coupler.

7. A method according to claim 6, wherein said driver further includes a radially recessed area proximal to the head of said driver that causes shearing of a portion of said driver proximal the head if excess torque is applied to said driver.

8. A method according to claim 6, wherein said implant-driver assembly is coupled to a superassembly by said coupler prior to use of said implant-driver assembly, wherein said coupler prevents axial movement between said implant-driver assembly and said superassembly.

9. An implant-driver assembly according to claim 1, wherein the plurality of fingers of said collar section of said coupler slide along the sloped surface of said flange to cause the plurality of fingers of said collar section, and the plurality of fingers of said implant engaging section to axially translate toward said driver head, thereby causing disengagement of said protruding portions of said plurality of fingers of said implant engaging section from the annular recess of said implant to cause said coupler to disengage from said implant to enable removal of said coupler and said driver from said implant.

10. A method according to claim 6, wherein the plurality of fingers of said collar section of said coupler slide along the sloped surface of said flange to cause the plurality of fingers of said collar section, and the plurality of fingers of said implant engaging section to axially translate toward said driver head, thereby causing disengagement of said protruding portions of said plurality of fingers of said implant engaging section from the annular recess of said implant to cause said coupler to disengage from said implant to enable removal of said coupler and said driver from said implant.

* * * * *